(12) United States Patent
Measamer

(10) Patent No.: US 8,500,629 B2
(45) Date of Patent: Aug. 6, 2013

(54) ENDOSCOPIC DEVICE

(75) Inventor: John P. Measamer, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1491 days.

(21) Appl. No.: 11/742,110

(22) Filed: Apr. 30, 2007

(65) Prior Publication Data

US 2008/0269566 A1 Oct. 30, 2008

(51) Int. Cl.
*A61B 1/005* (2006.01)
(52) U.S. Cl.
USPC ........................................................ 600/139
(58) Field of Classification Search
USPC ................................. 600/204, 139, 141–144
See application file for complete search history.

(56) References Cited

U.S. PATENT DOCUMENTS

| | | | |
|---|---|---|---|
| 3,946,727 A | 3/1976 | Okada et al. | |
| 3,948,251 A | 4/1976 | Hosono | |
| 5,549,542 A | 8/1996 | Kovalcheck | |
| 6,375,650 B1 * | 4/2002 | Ouchi | 606/1 |
| 6,458,075 B1 | 10/2002 | Sugiyama et al. | |
| 6,503,193 B1 | 1/2003 | Iwasaki et al. | |
| 6,520,214 B1 | 2/2003 | Sugiyama et al. | |
| 6,745,065 B2 | 6/2004 | Niwa et al. | |
| 2005/0080435 A1 | 4/2005 | Smith et al. | |
| 2005/0124912 A1 * | 6/2005 | Griego et al. | 600/564 |

* cited by examiner

*Primary Examiner* — Michael T Schaper
(74) *Attorney, Agent, or Firm* — Welsh Flaxman & Gitler LLC

(57) ABSTRACT

An endoscopic instrument for performing surgical procedures. The instrument includes an elongate member having a distal end for insertion into a patient's body and a proximal end opposite the distal end. The member has a distal portion adjacent the distal end and a central portion adjacent the distal portion. The distal portion has a first mechanical stiffness of a stiffness type selected from a tensile stiffness, a compressive stiffness and/or a bending stiffness. The central portion has a second mechanical stiffness of the stiffness type of the first mechanical stiffness. The first mechanical stiffness is different from the second mechanical stiffness.

15 Claims, 3 Drawing Sheets

ENDOSCOPIC DEVICE

BACKGROUND OF THE INVENTION

The present invention relates generally to an endoscopic device, and more particularly too an endoscopic device having differing mechanical properties along its length.

Endoscopic devices are medical devices use for examining and performing surgery inside a patient's body. Endoscopic devices typically include an elongate member for entering the body through a natural orifice or an incision and for extending into and through a body canal, an internal cavity or an organ so the interior of the body can be visually examined or operated upon without making large incisions in the patient. Endoscopic devices permit less invasive examination and surgeries than conventional examination and surgical methods.

It is envisioned it may be desirable for some portions of endoscopic devices to have different mechanical properties than the mechanical properties of other portions. For example, it may be desirable for a distal portion of an endoscopic device to be stiffer or less stiff than other portions of the device. More particularly, certain endoscopic devices known as endoscopic tissue manipulators or endoscopic tissue retractors may benefit from some portions of the device having different mechanical properties. As shown in U.S. Patent Application Publication No. 2005/0080435 A1, entitled, "Tissue Retractor and Method for Using the Retractor," filed Dec. 5, 2003, endoscopic tissue retractors include a flexible shaft made from coiled wire surrounded by a heat shrinkable polymer outer sleeve and having an end cap. Hooks positioned inside the coil are extendable through the end cap. The end of the retractor is positioned adjacent tissue the operator desires to manipulate when the hooks are retracted. Then the hooks are extended through the end cap. Because the hooks move along opposite arcs as they extend, the hooks pierce the tissue and engage the tissue as they are extended to attach the end of the manipulator to the tissue. Once the hooks engage the tissue, the manipulator may be retracted or otherwise moved to manipulate the tissue into a desired position. As will be appreciated by those skilled in the art, extending the hooks causes the coil forming a portion of the outer casing to be put in tension. If the tensile loads are great enough, the end of the coil can become stretched, thereby affecting its operation. To prevent strands of the coil at the end manipulator from stretching in tension when the hooks are extended, it is desirable for the end of the coil to be stiffer in tension than the rest of the coil. Under some circumstances, it is also envisioned that it may be desirable for the distal portion of the endoscopic manipulator to be stiffer in bending than the remainder of the manipulator. In some cases, having a stiffer end portion would allow for easy movement of the manipulator within a working channel, yet provide a stiffer device when positioning the hooks and engaging tissue.

Tensile loads may also be created in other types of endoscopic equipment. For example, as will be appreciated by those skilled in the art, endoscopic scissors may have tensile loading as they are opened due to preloads within the scissors mechanism needed for the scissors to function. In addition, endoscopic stapling devices that use fasteners stored in the device in their deformed shape may have significant tensile loading caused by the restoring forces of the staples on their confinement chamber.

SUMMARY OF THE INVENTION

Briefly, the present invention includes an endoscopic instrument for performing surgical procedures. The instrument comprises an elongate member having a distal end for insertion into a patient's body and a proximal end opposite the distal end. The elongate member has a distal portion adjacent the distal end and a central portion adjacent the distal portion. The distal portion has a first mechanical stiffness of a stiffness type selected from a group of stiffness types including a tensile stiffness, a compressive stiffness and a bending stiffness, and the central portion has a second mechanical stiffness of the stiffness type of the first mechanical stiffness. The first mechanical stiffness is different from the second mechanical stiffness.

In another aspect, the invention includes an endoscopic instrument for performing surgical procedures. The instrument comprises an elongate tubular sleeve having a hollow interior, a distal end for insertion into a patient's body, a proximal end opposite the distal end, a distal portion adjacent the distal end, and a central portion adjacent the distal portion. The instrument also includes an insert disposed within the hollow interior of the tubular sleeve for movement relative to the sleeve between a first position and a second position. The insert has a distal portion generally corresponding to the distal portion of the sleeve and a central portion adjacent the distal portion. The distal portion of the sleeve has a mechanical stiffness different from its central portion.

Other features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
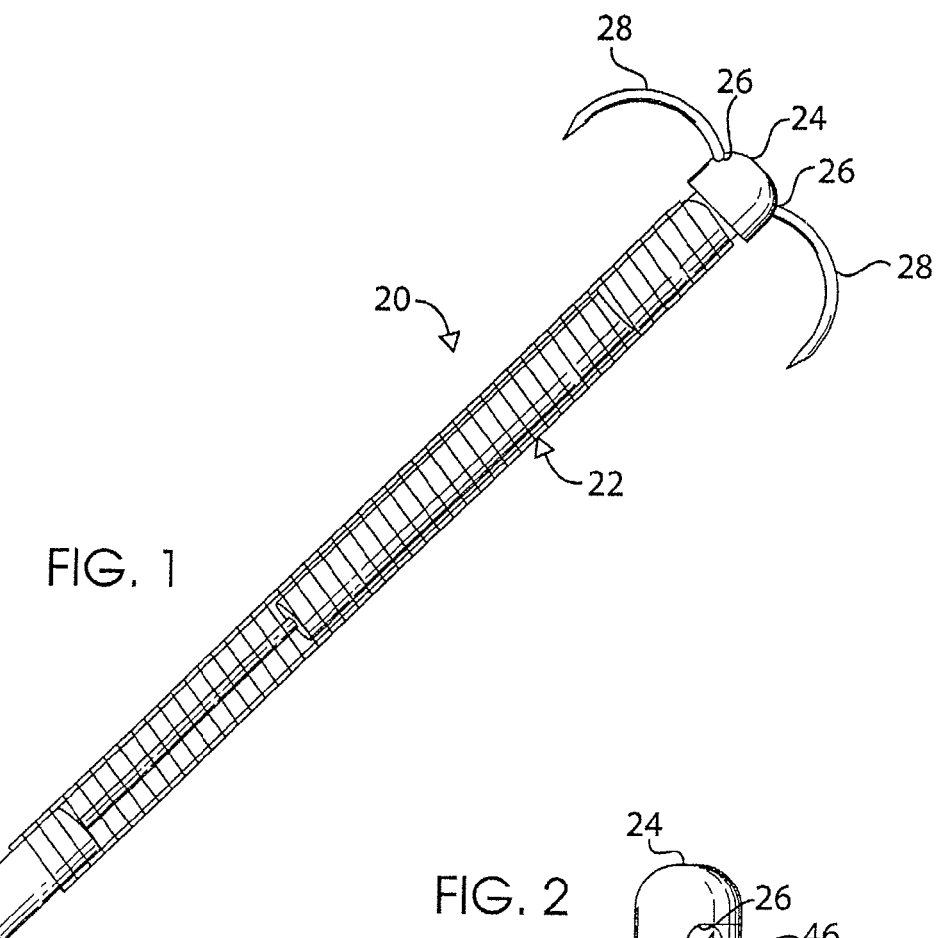
FIG. 1 is a side elevation of an end of an endoscopic tissue manipulator of a first embodiment of the present invention.

Referring now to the drawings and in particular to FIG. 1, an endoscopic instrument such as an endoscopic tissue manipulator is designated in its entirety by the reference numeral 20. The manipulator 20 includes a flexible shaft, generally designated by 22, having an end cap 24. One or more holes 26 are positioned around the end cap 24. Retractable hooks or needles 28 extend through the holes 26 for piercing tissue (not shown) as described in the background so the tissue can be positioned during endoscopic surgery. Although the end cap 24 may have fewer or more holes 26 and hooks 28, in one embodiment the end cap has two holes positioned on opposite sides of the cap and one hook corresponding to each hole. The end cap 24 may be attached to the shaft 22 in a conventional manner. For example, the end cap 24 may be attached by brazing, soldering, welding, press-fitting, swaging, adhesively bonding, screw fastening and/or combinations of these methods. In use, the end cap 24 is positioned adjacent tissue (not shown) a user intends to manipulate. The user extends the hooks 28 so they pierce the tissue. The manipulator 20 is moved (e.g., pulled) so the tissue is moved to a desired location. The hooks 28 are retracted to release the tissue.

Figure 2:
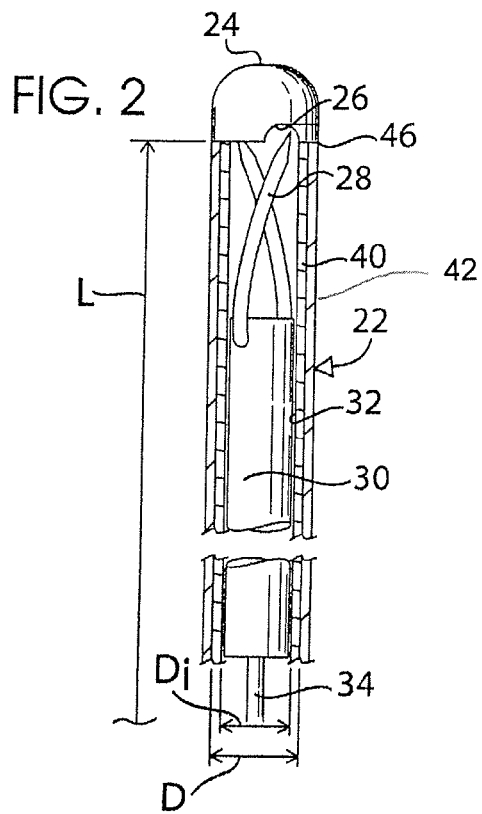
FIG. 2 is a cross section of the endoscopic tissue of the first embodiment.

As illustrated in FIG. 2, the hooks 28 are mounted on an actuator rod or connector 30 received within a hollow interior 32 of the flexible shaft 22. In one embodiment, the hooks 28 are pivotally attached to the connector 30. The connector 30 is attached to an actuation wire 34 which drives the connector 30 and hooks 28 between a retracted position shown in FIG. 2 and an extended position shown in FIG. 1. The wire 34 may be driven between these positions by any conventional actuation mechanism (not shown). For example, the wire 34 may be driven between these positions by a plunger mechanism as described in U.S. Patent Application Publication No. 2005/0080435 A1. Alternatively, the actuation mechanism may be a conventional lever mechanism commonly used in endoscopic stapling devices or other conventional mechanisms (not shown). The device 20 may also include a stop (not shown) for limiting movement of the hooks 28 beyond the retracted position. The hooks 28, connector 30 and wire 34 form an insert disposed in the hollow interior 32 of the flexible shaft 22 for movement relative to the shaft. Other internal mechanisms and features of the device are conventional and will not be described in detail herein.

Figure 3:
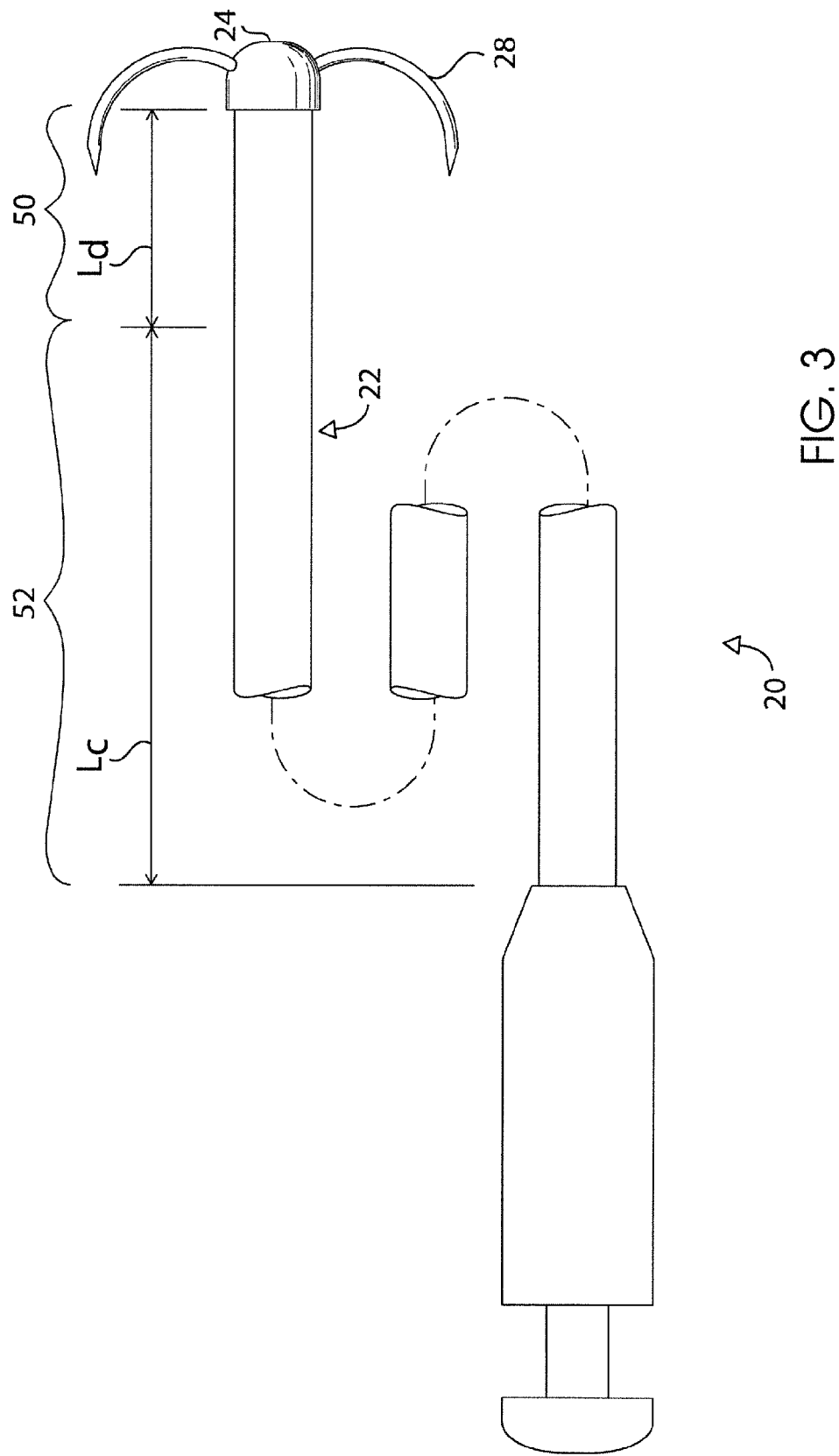
FIG. 3 is a side elevation of an endoscopic tissue manipulator as shown with reference to FIG. 2.

As illustrated in FIG. 2, the flexible shaft 22 includes a sleeve formed from an elongate helical coil 40. Although the coil 40 may be made of other materials without departing from the scope of the present invention, in one embodiment the coil 40 is made of stainless steel or nitinol available from Lake Region Manufacturing, Inc. of Chaska, Minn. In one embodiment, the coil 40 is sheathed with a flexible tubular cover 42, providing a smooth outer cover. Although the coil 40 may have other dimensions without departing from the scope of the present invention, in one embodiment the coil has an overall outer diameter D of between about 0.04 inch and about 0.16 inch, and an overall length L (FIG. 3) of between about sixty inches and about 100 inches. In one embodiment, the coil 40 has an inner diameter $D_i$ of between about 0.02 inch and about 0.145 inch. As further illustrated in FIG. 3, the flexible shaft 22 forms an elongate member having a distal end 44 for insertion into a patient's body (not shown) and a proximal end 46 opposite the distal end. Further, the shaft 22 has a distal portion, generally designated by 50, adjacent the distal end 44 and a central portion, generally designated by 52, adjacent the distal portion. The distal portion 50 has a first mechanical property that is different from the mechanical property of the central portion 52. More particularly, in one embodiment the distal portion 50 has a first mechanical stiffness that is different from the mechanical stiffness of the central portion 52. The mechanical stiffness may be a tensile stiffness, a compressive stiffness and/or a bending stiffness. In one embodiment, the mechanical stiffness of the distal portion 50 is greater than the mechanical stiffness of the central portion 52. In a more particular embodiment, these mechanical stiffnesses are bending stiffnesses. In other words, the bending stiffness of the distal portion 50 is greater than the bending of the central portion 52. In this embodiment, the tensile stiffness and compressive stiffness of the distal portion 50 and the central portion 52 are approximately the same. In another embodiment, the tensile stiffness and compressive stiffness of the distal portion 50 are also greater than the tensile stiffness and compressive stiffness of the central portion 52. Although the coil 40 is described as having differing mechanical properties in a distal portion 50 and a central portion 52, those skilled in the art will appreciate that other portions of the shaft 22 may have differing properties without departing from the scope of the present invention.

Although the distal portion 50 may have other lengths without departing from the scope of the present invention, in one embodiment the distal portion has a length $L_d$ of between about one inch and about six inches. Although the central portion 52 may have other lengths without departing from the scope of the present invention, in one embodiment the central portion has a length $L_c$ of between about 59 inches and about 100 inches. Although the distal portion 50 may have other lengths without departing from the scope of the present invention, in one embodiment the distal portion has a length $L_d$ that is between about one percent and about ten percent of the length $L_c$ of the central portion 52. Although the distal portion 50 may have other lengths without departing from the scope of the present invention, in one embodiment the distal portion has a length $L_d$ that is between about twenty times and about 150 times overall outer diameter D of the coil 40 at the distal portion. Although the distal portion 50 and the central portion 52 may have different diameters without departing from the scope of the present invention, in one embodiment the diameter is generally uniform along the entire length of the coil 40 along both the distal portion and central portion.

The stiffnesses of the distal portion 50 may be made to be different from the stiffnesses of the central portion 52 using several different methods. For example, in one embodiment, the distal portion 50 and the central portion 52 are made from different materials having differing mechanical properties. For example, the distal portion 50 may be made of nitinol or titanium and the central portion 52 may be made of stainless steel, thereby providing different material properties such as different stiffnesses for the different portions of the coil 40.

Although the distal portion 50 of the coil 52 may have other stiffnesses without departing from the scope of the present invention, in one embodiment the distal portion of the coil has a stiffness in tension of between about five pounds force per inch (lbf/in) and about twenty lbf/in, and a stiffness in bending of between about 0.02 lbf/in and about 0.40 lbf/in. Because the coils are close wound in one embodiment, the stiffness in compression is substantially greater than in tension or in bending. Although the central portion 52 of the coil 40 may have other stiffnesses without departing from the scope of the present invention, in one embodiment the central portion of the coil has a stiffness in tension of between about five lbf/in and about twenty lbf/in, a much larger stiffness in compression, and a stiffness in bending of between about 0.02 lbf/in and about 0.40 lbf/in. Although the ranges of stiffnesses of the distal portion 50 and the central portion 52 of the coil 40 are the same, the particular value of the stiffness chosen from the range is different for each portion.

Figure 4:
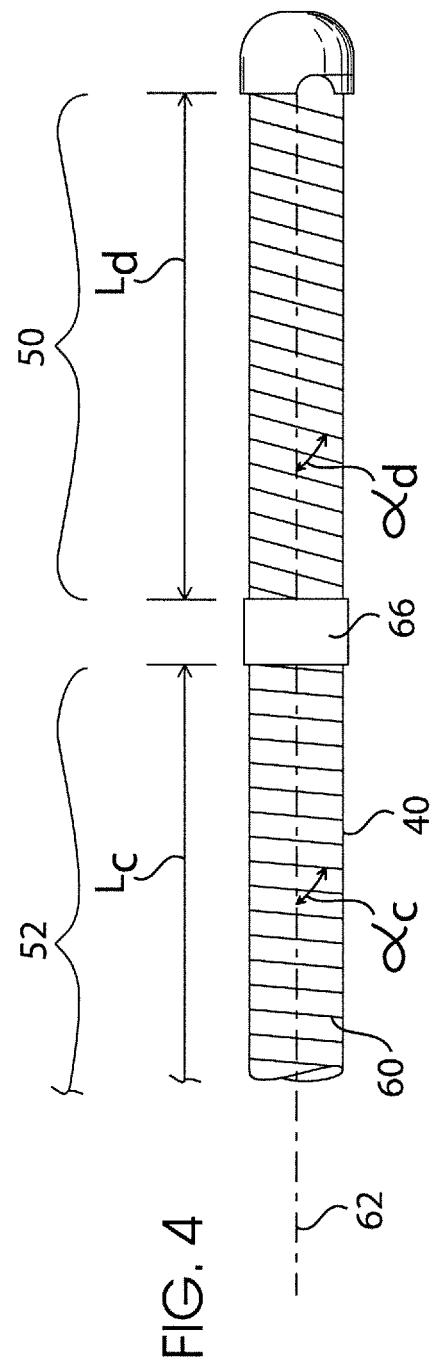
FIG. 4 is a cross section of an endoscopic tissue manipulator of a second embodiment of the present invention.

As illustrated in FIG. 4, the coil 40 of a second embodiment is formed by a strand 60 (i.e., one or more strands) wrapped in a helix around an imaginary longitudinal axis 62. The strand 60 has a different pitch along the distal portion 50 of the coil than along the central portion 52 of the coil to provide the differing mechanical properties. The pitch along the distal portion 50 of the coil 40 is defined by a helix angle $\alpha_d$ measured between the strand and the longitudinal axis 62 of the coil 40, and the pitch in the central portion 52 is defined by a helix angle $\alpha_c$ measured between the strand and the longitudinal axis of the coil. As shown in FIG. 4, the angle $\alpha_d$ along the distal portion 50 of the coil 40 is between about six degrees and about fifteen degrees, and the angle $\alpha_c$ in the central 52 of the coil is between about one degree and about fifteen degrees, resulting in the distal portion 50 of the coil being stiffer in tension, compression and bending. Although the coil 40 may be made of other materials without departing from the scope of the present invention, in one implementation of the second embodiment, both the distal portion 50 and the central portion 52 of the coil are made of stainless steel or nitinol. In alternative implementations of the second embodiment, the distal portion 50 of the coil 40 may be made of a different material than the central portion 52 of the coil.

Although the distal portion 50 and the central portion 52 of the coil 40 may be joined in other ways without departing from the scope of the present invention, in one embodiment the distal portion and central portion are mechanically joined by a band 66. The distal portion 50 and central portion 52 of the coil may be connected to the band 66 in any conventional manner such by brazing, soldering, welding, swaging, adhesively bonding and/or press fitting. Alternatively, the coil 40 may be formed as one piece or the distal portion 50 and the central portion 52 of the coil may be separately formed and joined by conventional techniques such as welding.

Figure 5:
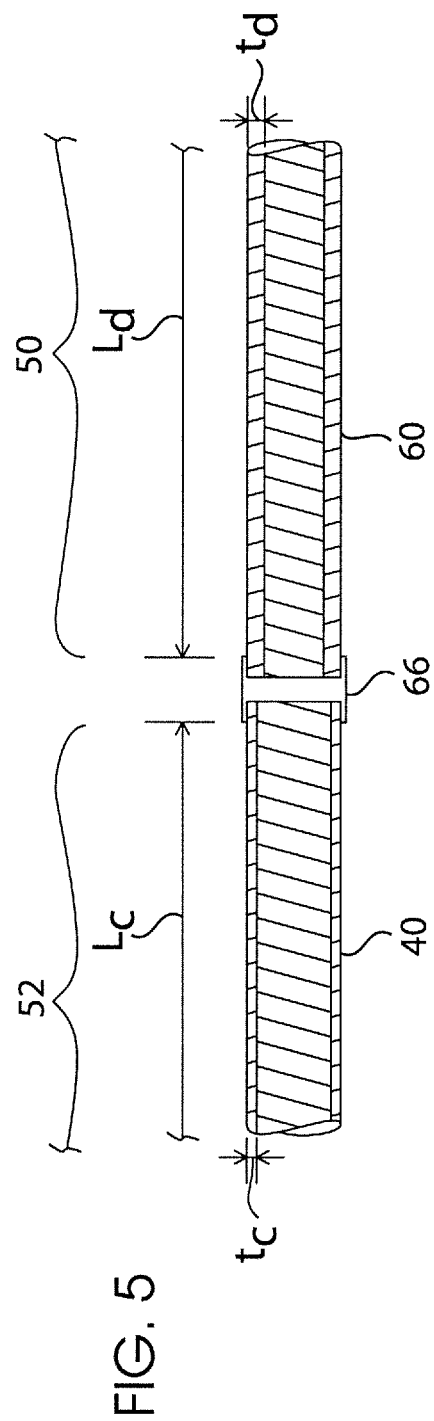
FIG. 5 is a cross section of an endoscopic tissue manipulator of a third embodiment of the present invention.

As illustrated in FIG. 5, in a third embodiment the strand 60 forming the coil 40 has different cross sectional dimensions in the distal portion 50 and the proximal portion 52. For example, in one embodiment shown in FIG. 5 the strand 60 of the distal portion 50 of the coil 40 has a thickness $t_d$ that is larger than a thickness $t_c$ of the strand at the central portion 52 of the coil. In other embodiments (not shown), a width $w_d$ of the distal portion 50 of the coil 40 may be different from a width $w_c$ of the central portion 52 of the coil. Alternatively, the distal portion 50 and/or the central portion 52 of the coil may be covered with a stiffener (not shown) to achieve an increased effective thickness and resulting stiffness. Although the strand have other cross-sectional shapes without departing from the scope of the present invention, in one embodiment the strand has a rectangular cross section.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An endoscopic instrument for performing surgical procedures, said instrument comprising:
    an elongate member having a distal end for insertion into a patient's body and a proximal end opposite the distal end, the member having a distal portion adjacent the distal end and a central portion adjacent the distal portion;
    wherein the distal portion has a first mechanical stiffness being a stiffness in tension of between about 5 lbf/in and about 20 lbf/in and a stiffness in bending of between about 0.02 lbf/in and about 0.40 lbf/in, and the central portion has a second mechanical stiffness being a stiffness in tension of between about 5 lbf/in and about 20 lbf/in and a stiffness in bending of between about 0.02 lbf/in and about 0.40 lbf/in; and
    wherein the first mechanical stiffness is greater than the second mechanical stiffness.

2. An instrument as set forth in claim 1 wherein the member comprises an elongate coil at the distal portion of the member and the central portion of the member.

3. An instrument as set forth in claim 2 wherein the coil has a different pitch in the distal portion of the member than in the central portion of the member.

4. An instrument as set forth in claim 2 wherein the coil comprises a strand wrapped in a helix and the strand has different cross sectional dimensions in the distal portion of the member than in the central portion of the member.

5. An instrument as set forth in claim 4 wherein the strand has a width extending longitudinally with respect to the elongate member and a thickness extending laterally with respect to the elongate member, and wherein the width of the strand in the distal portion of the member is greater than the width of the strand in the central portion of the member.

6. An instrument as set forth in claim 4 wherein the strand forms a helix angle with respect to a central axis of the elongate member, and wherein the helix angle of the strand in the distal portion of the member is less than the helix angle of the strand in the central portion of the member.

7. An instrument as set forth in claim 4 wherein the strand is mechanically joined between the distal portion and the central portion of the elongate member.

8. An endoscopic instrument for performing surgical procedures, said instrument comprising:
    an elongate tubular sleeve having a hollow interior, a distal end for insertion into a patient's body, a proximal end opposite the distal end, a distal portion adjacent the distal end, and a central portion adjacent the distal portion; and
    an insert disposed within the hollow interior of the tubular sleeve for movement relative to the sleeve between a first position and a second position, said insert having a distal portion generally corresponding to the distal portion of the sleeve and a central portion adjacent the distal portion of the insert;
    wherein the distal portion of the sleeve has a first mechanical stiffness being a stiffness in tension of between about 5 lbf/in and about 20 lbf/in and a stiffness in bending of between about 0.02 lbf/in and about 0.40 lbf/in and the central portion has a second mechanical stiffness being a stiffness in tension of between about 5 lbf/in and about 20 lbf/in and a stiffness in bending of between about 0.02 lbf/in and about 0.40 lbf/in; and wherein the first mechanical stiffness is greater than the second mechanical stiffness.

9. An instrument as set forth in claim 8 wherein the sleeve comprises an elongate coil at the distal portion of the sleeve and the central position of the sleeve.

10. An instrument as set forth in claim 9 wherein the coil has a different pitch in the distal portion of the member than in the central portion of the member.

11. An instrument as set forth in claim 9 wherein the coil comprises a strand wrapped in a helix and the strand has different cross sectional dimensions in the distal portion of the sleeve than in the central portion of the sleeve.

12. An instrument as set forth in claim 11 wherein the strand has a width extending longitudinally with respect to the elongate sleeve and a thickness extending laterally with respect to the elongate sleeve, and wherein the width of the strand in the distal portion of the sleeve is greater than the width of the strand in the central portion of the sleeve.

13. An instrument as set forth in claim 11 wherein the strand forms a helix angle with respect to a central axis of the elongate member, and wherein the helix angle of the strand in the distal portion of the member is less than the helix angle of the strand in the central portion of the member.

14. An instrument as set forth in claim 11 wherein the strand is mechanically joined between the distal portion and the central portion of the elongate sleeve.

15. An instrument as set forth in claim 8 wherein the instrument is an endoscopic tissue manipulator.

\* \* \* \* \*